(12) United States Patent
Boock et al.

(10) Patent No.: US 6,620,179 B2
(45) Date of Patent: Sep. 16, 2003

(54) CLOT DISRUPTING WIRE/CATHETER ASSEMBLY

(75) Inventors: Robert Boock, Minnetonka, MN (US); Jeffrey A. Lee, Plymouth, MN (US)

(73) Assignee: NeuroVasx, Inc., Maple Grove, MN (US)

( * ) Notice: Subject to any disclaimer, the term of this patent is extended or adjusted under 35 U.S.C. 154(b) by 0 days.

(21) Appl. No.: 09/867,270

(22) Filed: May 29, 2001

(65) Prior Publication Data

US 2002/0032455 A1 Mar. 14, 2002

Related U.S. Application Data

(63) Continuation-in-part of application No. 09/371,267, filed on Aug. 10, 1999.

(51) Int. Cl.$^7$ .............................................. A61B 17/22
(52) U.S. Cl. ...................................... 606/159; 606/171
(58) Field of Search ................................ 606/159, 127, 606/128, 170, 167, 171, 180, 20; 600/564

(56) References Cited

U.S. PATENT DOCUMENTS

| | | | | | |
|---|---|---|---|---|---|
| 4,832,055 | A | * | 5/1989 | Palestrant | 128/899 |
| 5,669,936 | A | * | 9/1997 | Lazarus | 606/195 |
| 5,792,156 | A | * | 8/1998 | Perouse | 604/96.01 |
| 5,972,019 | A | * | 10/1999 | Engelson et al. | 606/159 |
| 6,113,615 | A | * | 9/2000 | Wulfman | 606/159 |
| 6,152,932 | A | * | 11/2000 | Ternstrom | 606/113 |

* cited by examiner

*Primary Examiner*—Pedro Philogene
(74) *Attorney, Agent, or Firm*—Schwegman, Lundberg, Woessner & Kluth, P.A.

(57) ABSTRACT

The present invention includes a clot disrupting wire/catheter assembly. The clot disrupting wire/catheter assembly comprises an annular sleeve and a core wire that is positioned within the annular sleeve. The assembly also includes a distal end wire that is attached to the annular sleeve and the core wire.

24 Claims, 17 Drawing Sheets

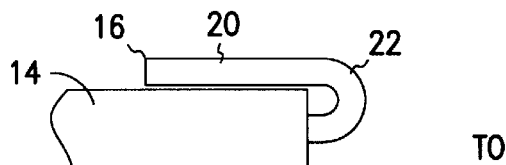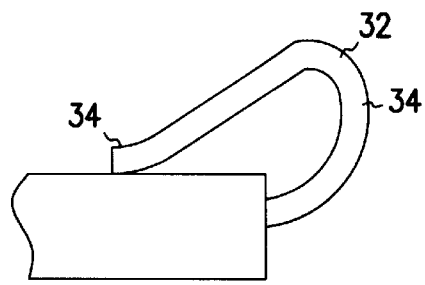
FIG. 3A    TO    FIG. 3B
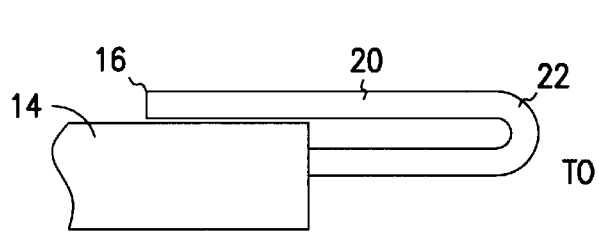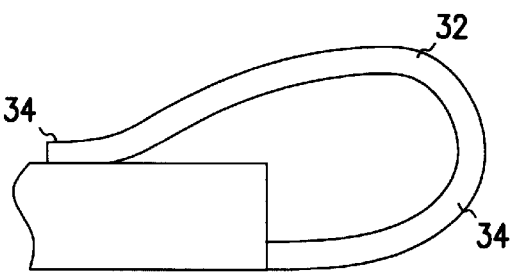
FIG. 4    TO    FIG. 4B
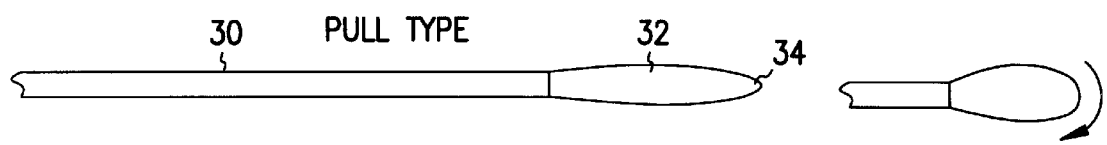
FIG. 4A

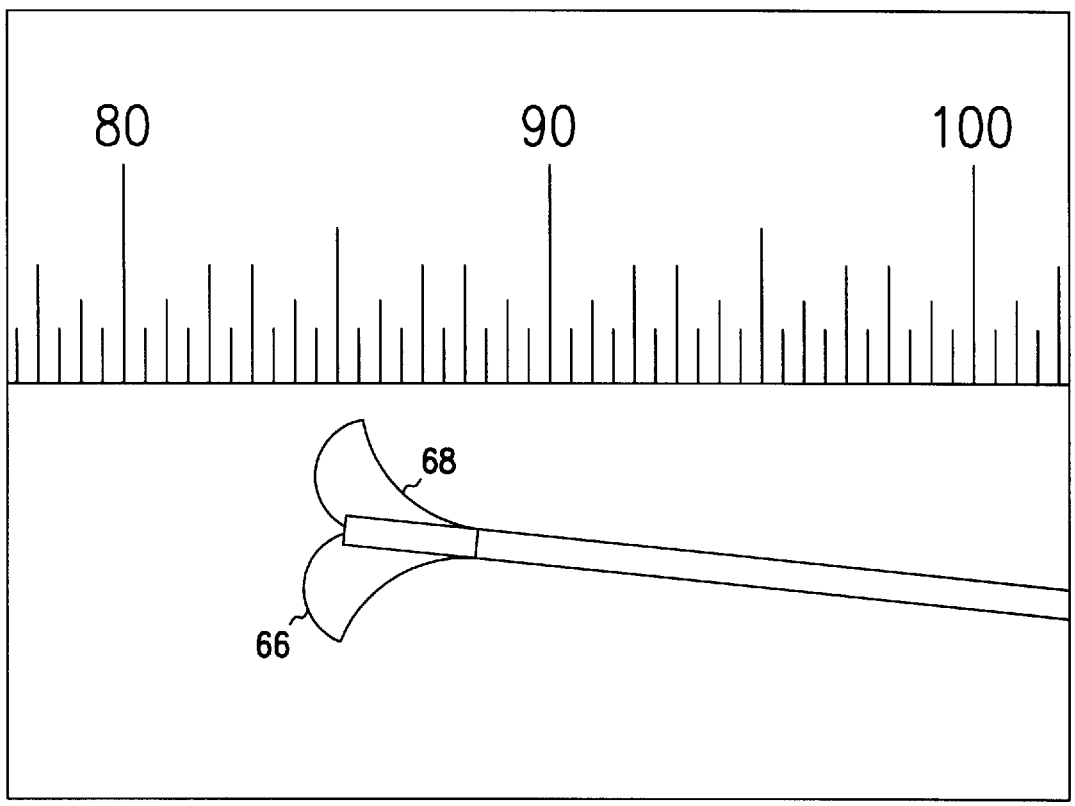
FIG. 6A
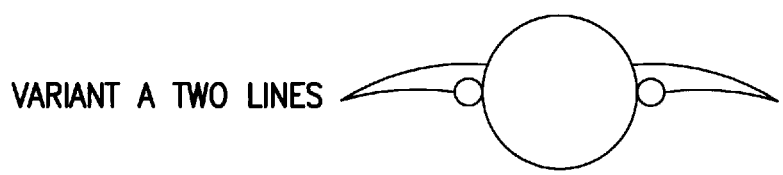
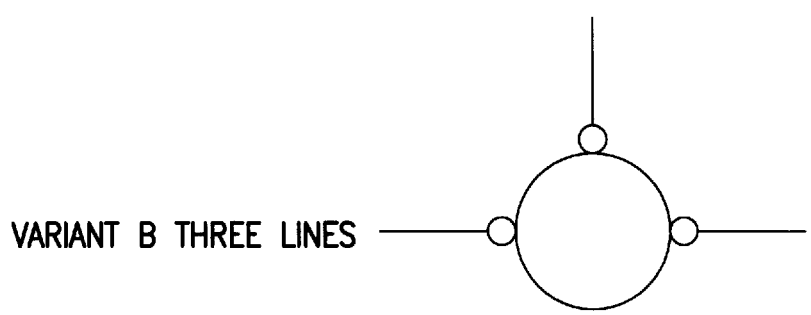 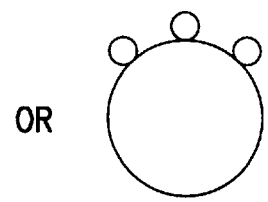
FIG. 7A  FIG. 7B

US 6,620,179 B2

CLOT DISRUPTING WIRE/CATHETER ASSEMBLY

This application is a continuation-in-part of U.S. Ser. No. 09/371,267, filed Aug. 10, 1999.

BACKGROUND OF THE INVENTION

The present invention relates to a macerating wire assembly and to a method for macerating a thrombus.

Brain attack afflicts more than 700,000 people in the United States annually. About 70 to 85% of brain attack episodes are attributable to ischemic stroke, which carries a mortality of 15–33%. Emerging treatments for acute cerebral ischemia include thrombolytic treatment. One type of thrombolytic treatment involves an early use of clot lysing agents and a subsequent restoration of blood flow. One lysing agent, rt-PA has been shown to be effective in restoring circulation and in reducing the overall morbidity. However, the benefits of rt-PA are effective only if treatment begins within the first 90 minutes to 3 hours after the initial ictus.

Currently, trials are underway to reduce the complications associated with this treatment by using local intra-arterial versus systemic intravenous delivery as well as the potential use of other low cost alternative thrombolytic agents. There have also been advances in imaging technologies such as perfusion MRI, CT angiography, and advances in diagnostic blood tests all geared to the early diagnosis of stroke to speed treatment and expand the efficacy of these early interventions.

Other types of stroke treatment include early imaging, and a creation of dedicated stroke centers. All of these treatments have brought a greater emphasis the early treatment of stroke. A key to this treatment is a re-establishment of blood flow as early as possible to limit ischemic brain damage. The difficulty with thrombolysis alone is that this technique depends upon several variables, clot type, clot density, location, metabolism and so forth which adversely impact the effectiveness of this treatment.

Several devices have been designed for peripheral clot disruption. One device is described in U.S. Pat. No. 5,779,721 ('721), which issued Jul. 14, 1998. The '721 patent describes a system for opening a lumen in an occluded blood vessel. The system includes a working head for revascularizing the blood vessel and a mechanism for extracting or removing debris produced by operation of the working head. The working head is a rotary impacting impeller. The mechanism for extracting or removing debris introduces an infusate liquid into the blood vessel adjacent the working head and withdraws the liquid and some blood from the vessel. The infusate liquid may include a lytic drug such as heparin or urokinase. The blood and infusate liquid are remotely collected.

Thrombectomy devices may be utilized as a part of the system. One device is the Amplatz Thrombectomy Device designated by the trademark CLOT BUSTER by Microvena Corporation. Another device is the Craig Thrombectomy Brush.

SUMMARY OF THE INVENTION

One embodiment of the present invention includes a clot disrupting wire/catheter assembly. The clot disrupting wire/catheter assembly comprises an annular sleeve and a core wire that is positioned within the annular sleeve. A distal end wire is attached to the annular sleeve and the core wire.

Another embodiment of the present invention includes a method for clot disruption. The method comprises providing a clot disrupting assembly that comprises an annular sleeve, a core wire positioned within the annular sleeve and a distal end wire attached to the annular sleeve and the core wire. The method also includes pushing the core wire in order to deploy the distal end wire and positioning the distal end wire within a clot. Another method embodiment includes pulling the core wire in order to deploy the distal end wire and positioning the distal end wire within a clot.

One other embodiment of the present invention includes a kit for clot disruption. The kit comprises a main body defining a first lumen and a second lumen and a clot disrupting assembly positioned within or is integral with the first lumen. A lytic drug may be enclosed in the second lumen.

DESCRIPTION OF THE DRAWINGS

FIG. 3A is a side view illustrating distal wire contacts for a "push-out" clot disrupting device in an undeployed position.

FIG. 3B is a side view illustrating distal wire contacts for a "push-out" clot disrupting device embodiment in a deployed position.

FIG. 4 is a side view illustrating distal wire contacts for a "pull-in" clot disrupting device embodiment.

FIG. 4A is a side view illustrating distal wire contacts for a "pull-in" clot disrupting device embodiment in an undeployed position.

FIG. 4B is a side view illustrating distal wire contacts for the "pull-in" clot disrupting device in a deployed position.

FIG. 6A is a top view of a dual loop wire clot disrupting device embodiment of the present invention.

FIG. 7A is a radial cross-sectional view of one triple loop clot disrupting device wire embodiment.

FIG. 7B is a radial cross-sectional view of another triple loop clot disrupting wire embodiment of the present invention.

FIG. 12C-1 is a radial cross-sectional view of the dual loop embodiment of FIG. 12C.

FIG. 12D-1 is a radial cross-sectional view of the dual loop embodiment of FIG. 12D.

FIG. 12E-1 is a radial cross-sectional view of the triple loop embodiment of the clot disrupting wire of 12E.

FIG. 12F-1 is a radial cross-sectional view of another triple loop embodiment of the clot disrupting wire of the present invention.

DETAILED DESCRIPTION OF EMBODIMENTS

Figure 1:
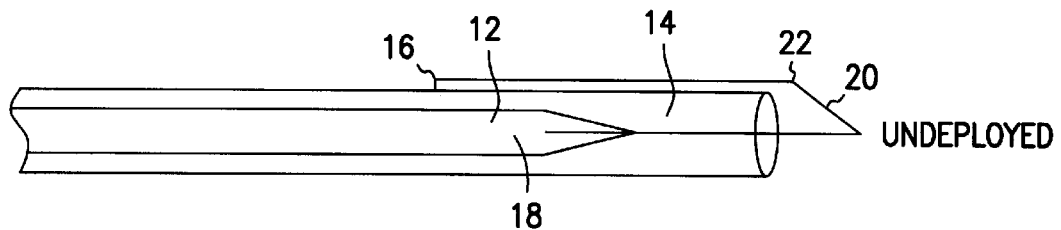
FIG. 1 is a transverse cross-sectional view of one embodiment of the wire loop clot disrupting device of the present invention in an undeployed position.
Figure 2:
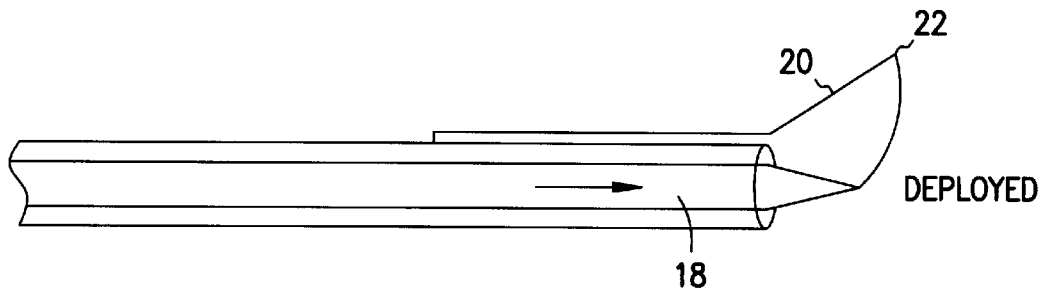
FIG. 2 is a transverse cross-sectional view of the embodiment of FIG. 1 in a deployed position.

One embodiment of the clot disruption wire/catheter assembly of the present invention, illustrated generally at 10 in FIG. 1 in an undeployed position, includes a wire 12 positioned within an annular sleeve 14, wherein the wire 12 is attached at a distal end 16 to the sleeve 14. The wire 12 comprises a core wire element 18 and a distal wire element 20 that may be integrally formed with the core wire 12 or may be attached to the core wire 12 by a procedure such as crimping. The wire element 20 can be memory conformed.

The clot disrupting wire/catheter assembly 10 is deployed by pushing the core wire 12 which releases the wire element 20 from the sleeve 14. Once released from the sleeve, the wire element 20 is deployed and expands outward due to its constrainment to the sleeve. This particular type of expanded conformation can be enhanced in wire 12 because a bend 22 could be memory-imparted to the distal wire element 20 which is close to the sleeve, as shown in FIGS. 3A and 3B.

Figure 3:
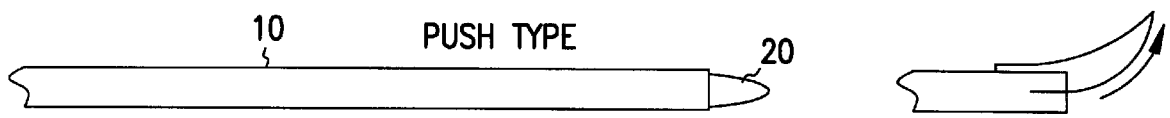
FIG. 3 is a side view of one embodiment of the wire loop clot disrupting device of the present invention.

The bend 22 expands the distal wire 20 as the wire is pushed as is shown in FIGS. 3A and 3B. This memory imparted bend 13 is not required for action but can enhance the performance of said device.

Another clot disrupting wire assembly 30, illustrated in FIG. 4, is deployed by pulling the core wire 12. The core wire 12 is attached to a distal wire element 32 by an attachment such as crimping. The core wire 12 may be integrally formed with the distal wire element 32 as well. The distal wire element 32 is attached at one end 34 to the sleeve 14. The distal wire 32 has a bend 34 that is positioned away from the sleeve as compared to the push-deployed assembly 10. As a consequence, pulling the core wire 12 causes the constrained distal wire 32 element to expand and to open up to a deployed position.

As used herein, the term "rest position" refers to a pre-set conformation of the wire element 20 or 32 of the guidewire assembly 10 or 30. The pre-set conformation may be an open, expanded conformation such as a single loop or a double loop or a triple loop, or may be a closed or partially closed conformation.

As used herein, the term "deployed" or "deployed position" refers to a distal loop formed by the wire element 20 or 32 in an open, expanded conformation. A deployed position is capable of macerating or recannulizing a thrombus.

Pushing or pulling the core wire 12 may cause deployment and thrombus disruption and channel formation within the thrombus depending upon the pre-set configuration of the distal wire element. When used in conjunction with a drug delivery system, such as an end hole infusion catheter (EHIC), the combination of thrombus disruption and drug delivery creates a channel for blood flow through the thrombus.

The core wire 12 may be fabricated from a biocompatable material such as stainless steel or Nitinol. The distal wire elements 20 and 32 are fabricated from a memory material such as Nitinol or other polymer-based memory material or other non-memory material that can retain a pre-set shape. It is further contemplated that the Nitinol wire or polymeric material may be coated. In one embodiment, the distal wire elements 20 and 32 are coated with a coating that comprises or that absorbs a lytic drug. With this embodiment, the lytic drug is delivered in intimate contact with the thrombus during thrombus disruption. In another embodiment, the wire or polymeric memory material is coated with an abrasive coating. The abrasive coating further aids in breaking up and dispersing a thrombus. In another embodiment, the wire is coated with a hydrophilic "slippery" coating which allows for less vessel wall damage.

Figure 5:
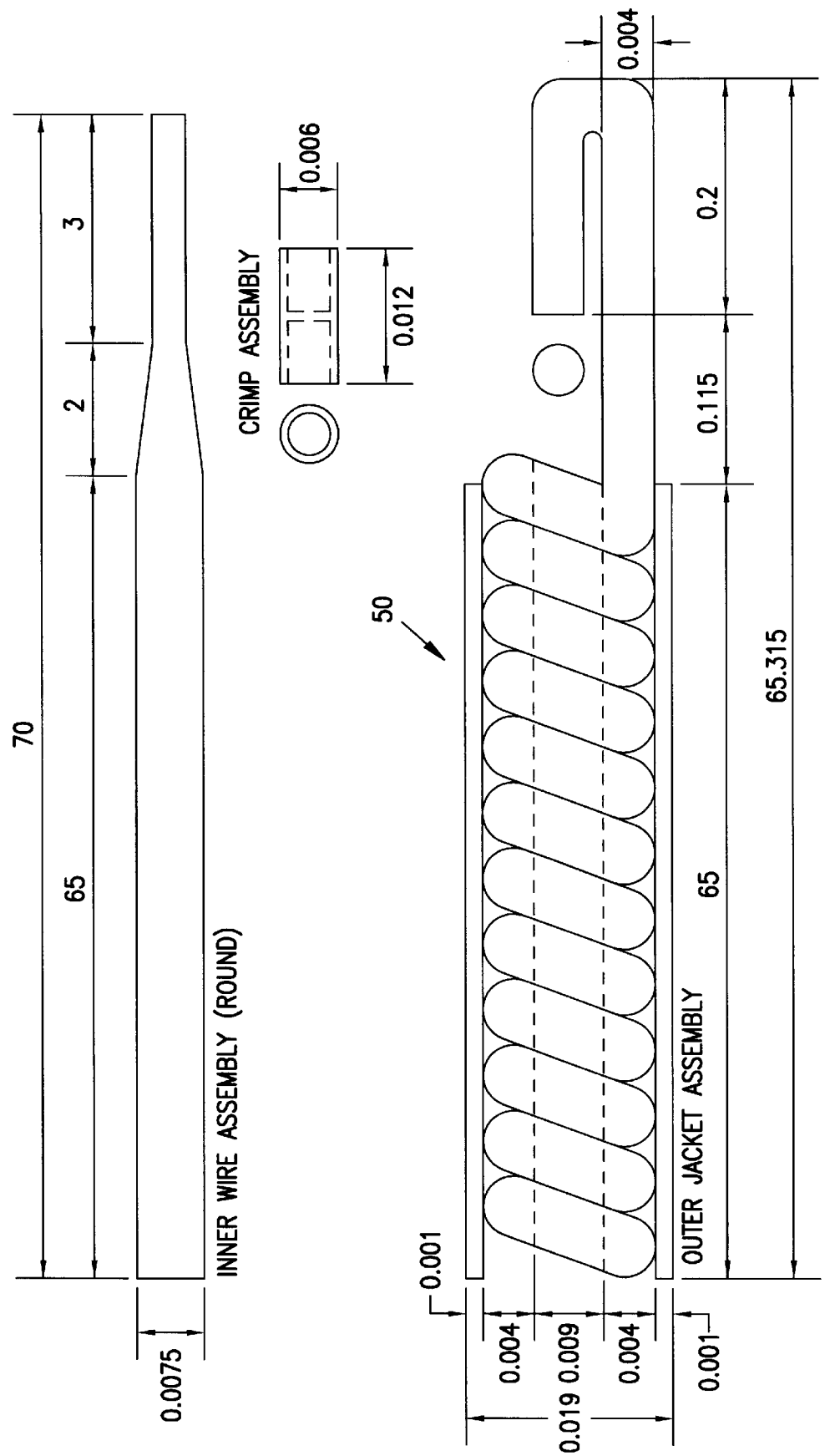
FIG. 5 is a side view of a coiled wire sleeve component of the clot disrupting device of the present invention.

The ends 16 and 34 of distal wires 20 and 32 are attached to the sleeve 14 by mechanisms such a gluing, positioning within an oversleeve, or embedding directly in the sleeve in an extrusion process or as part of a continuous coil sleeve or other conventional attachment mechanism. The sleeve 14 may be slotted for wire placement and then remelted to seal the wire into the sleeve. In another embodiment, the sleeve 14 comprises wire or polymeric coils, With this embodiment, the distal wire 20 or 32 extends from a distal coil such as is shown at 50 in FIG. 5.

Figure 6:
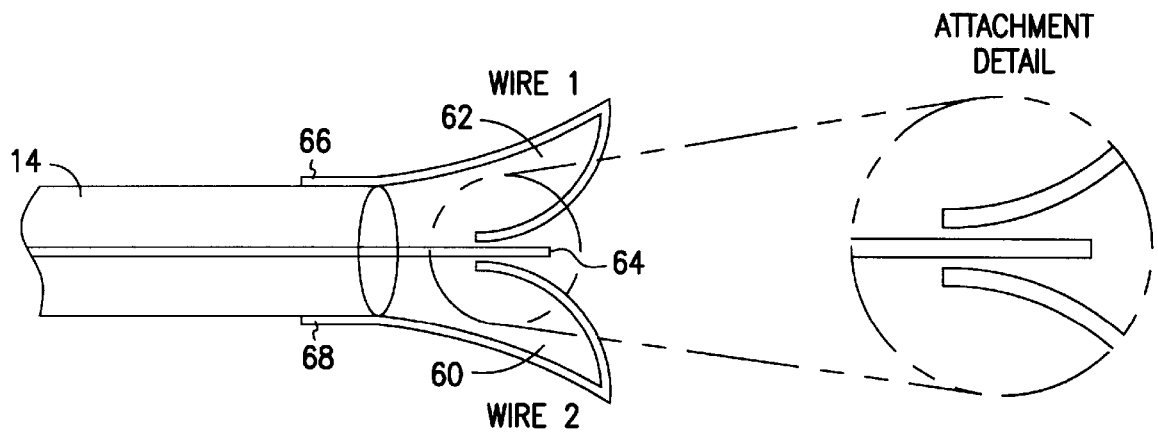
FIG. 6 is a transverse cross-sectional view of a dual loop clot disrupting device embodiment of the present invention.
Figure 6B:
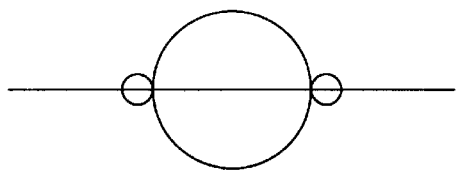
FIG. 6B is a radial cross-sectional view of one embodiment of the dual looped clot disrupting device of FIG. 6.
Figure 6C:
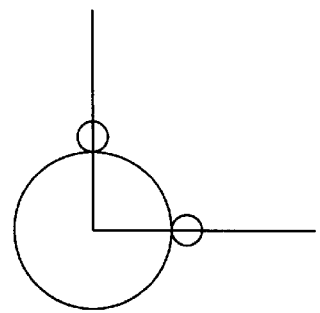
FIG. 6C is a radial cross-sectional view of one other embodiment of the dual looped clot disrupting device of FIG. 6.

The thrombus disrupting wire assembly may also include two or more wire loops at its distal end as is shown at 60 and 62 in FIG. 6. With this embodiment, the core wire 12 extends through the sleeve 14 and is bonded to distal wires 60, 62 at 64. The distal wires 60 and 62 are constrained to extend outward to form the bow that is shown in FIG. 6. Pushing the core wire 12 creates the bow forming two loops 60 and 62 shown in FIG. 6A. Ends of the distal wire 60 and 62 which are 66 and 68 may be attached to the sleeve in a variety of positions to obtain a variety of double or triple loop conformations. Ends of the embodiment of FIG. 6A are shown in cross-section in FIG. 6B. In another embodiment, the ends 66 and 68 are offset as shown in cross-section in FIG. 6C.

A third loop is created by attaching a third distal wire to the first and second distal wires as is shown in cross-section in FIG. 7A or 7B. These wires are attached to the core wire as described above.

Figure 8:
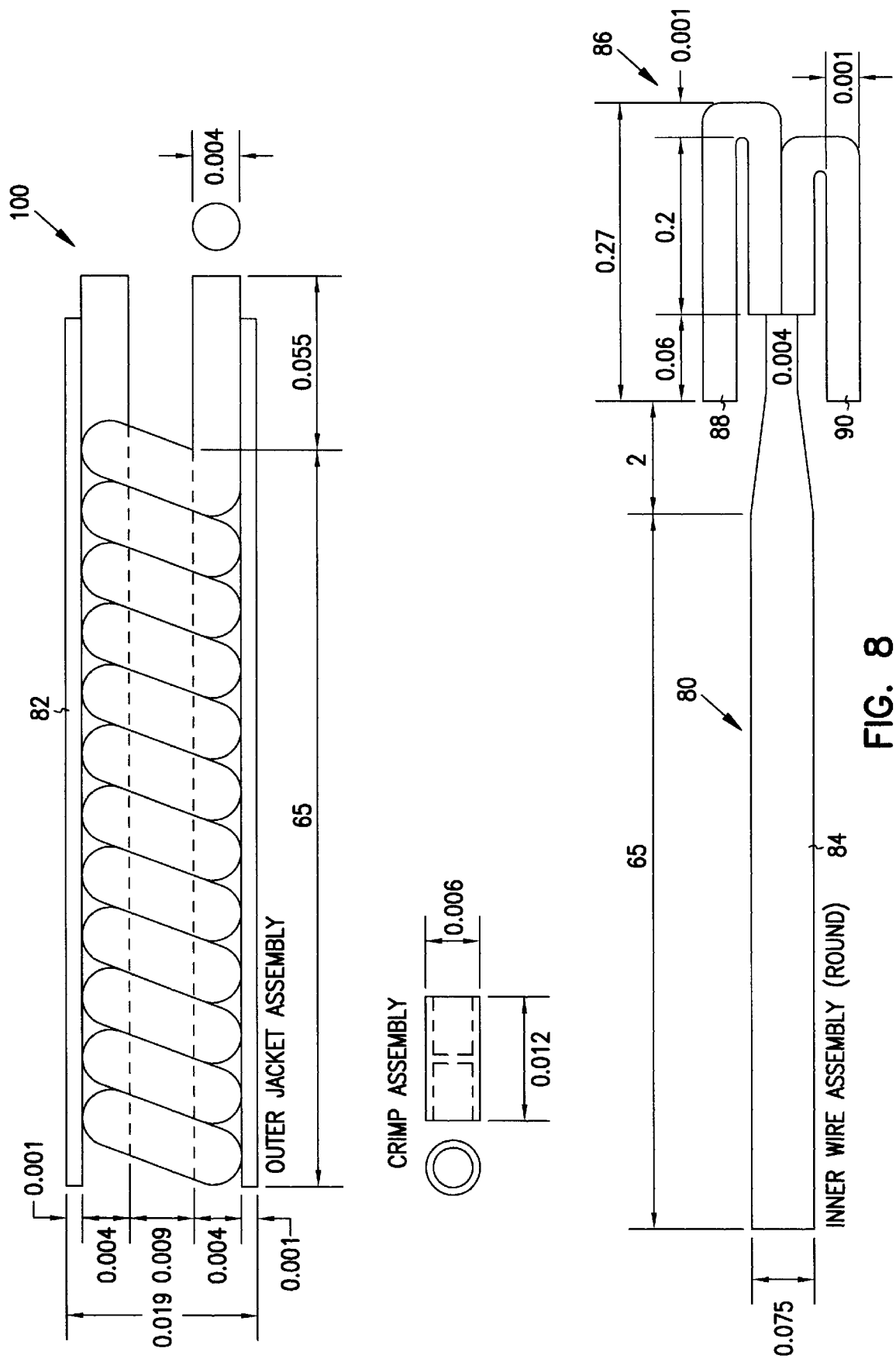
FIG. 8 is a side view of one embodiment of the "M" shaped distal wire embodiment of the present invention.
Figure 9:
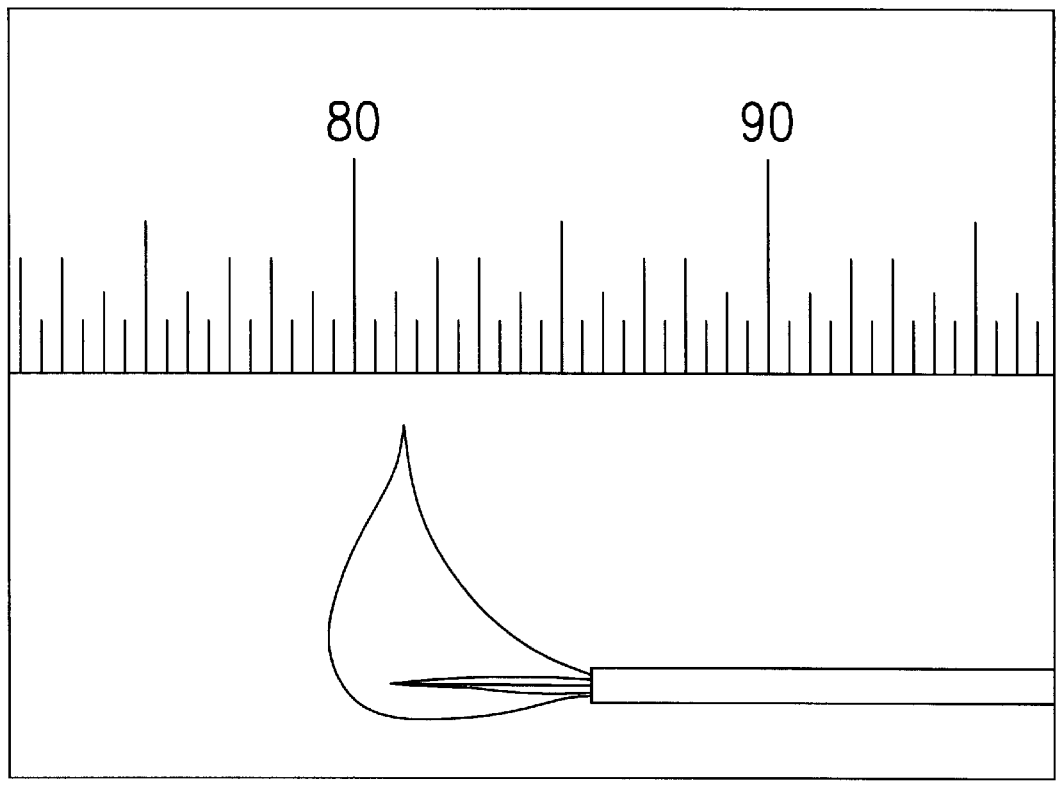
FIG. 9 is a top view of an offset "M" shaped distal wire embodiment.
Figure 10A:
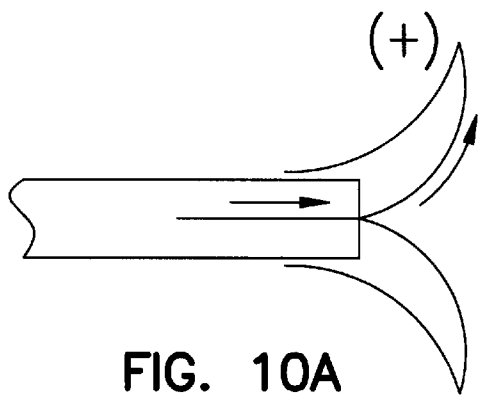
FIG. 10A is a side view of an "M" shaped distal wire in a positive conformation.
Figure 10B:
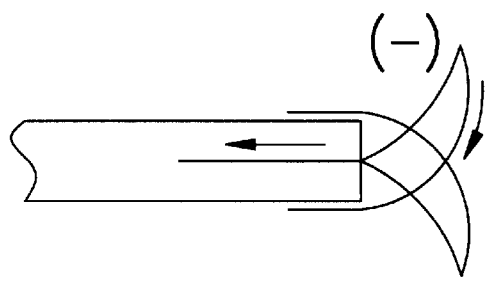
FIG. 10B is a side view of the embodiment of FIG. 10A in a negative conformation.

One dual loop embodiment, illustrated at 80 in FIG. 8, includes a sleeve 82 and a core wire 84 that is positioned within the sleeve 82. An M-shaped, continuous distal wire 86 is attached to the core wire 84 at a bottom of the M as shown in FIG. 8. Ends of the M-shape 88 and 90 are attached to the sleeve 82. The "M" shape may be an offset "M" with one tine of the distal wire smaller than the other tine. The "M" shape may also be a twisted "M" wherein one peak of the M is twisted in order to allow for 90 degree deployment and is shown in FIG. 9. With the "M" shaped embodiments, pushing the core wire 84 creates a positive deployment of the distal wire as shown in FIG. 10A. Pulling the core wire 84 creates a negative deployment as shown in FIG. 10B. The actions of pushing and pulling the core wire creates a two-dimensional, "scissors-like" motion. In another embodiment, a second "M" shaped distal wire is attached to the core wire 84 and the sleeve. Pushing and pulling this configuration produces an action like a three-dimensional, egg beater.

Figure 11:
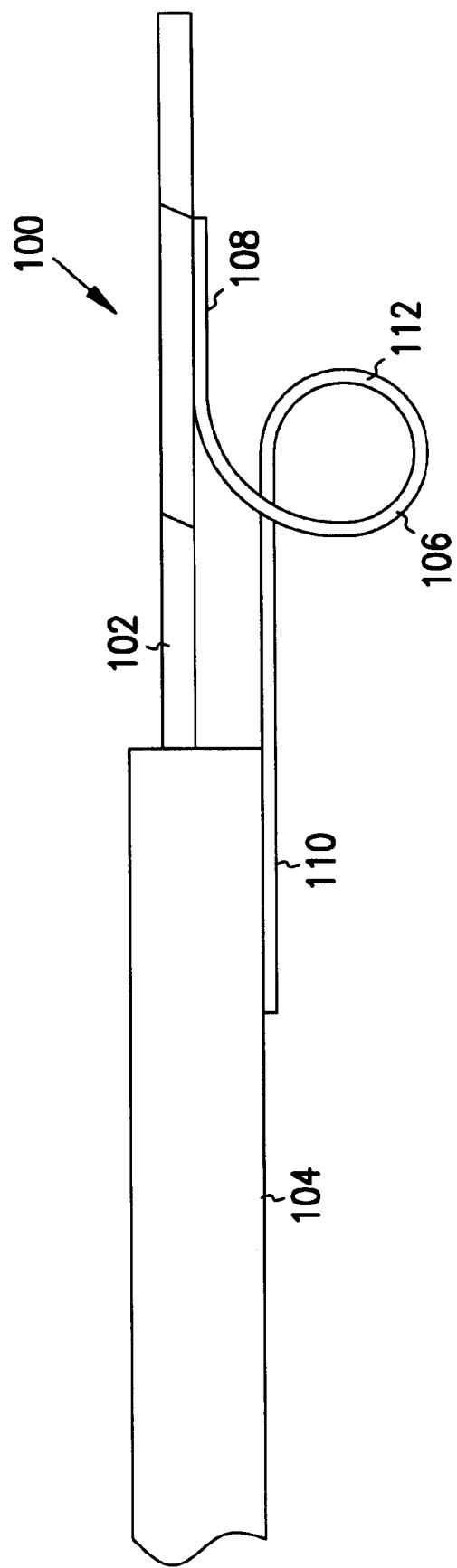
FIG. 11 is a side view of a looped distal wire embodiment of the present invention.
Figure 11A:
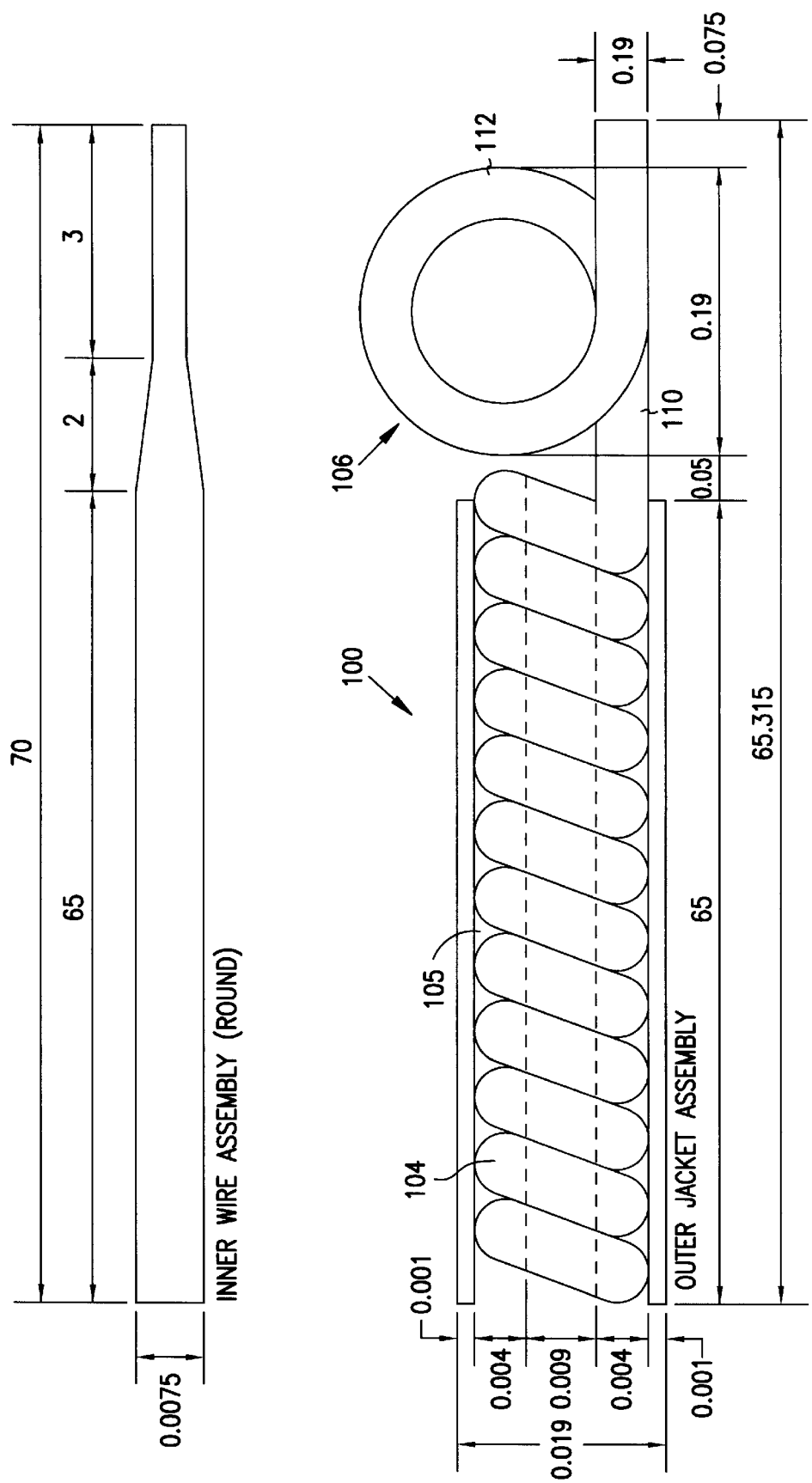
FIG. 11A is a cross-sectional view of one other looped distal wire embodiment of the present invention.
Figure 11B:
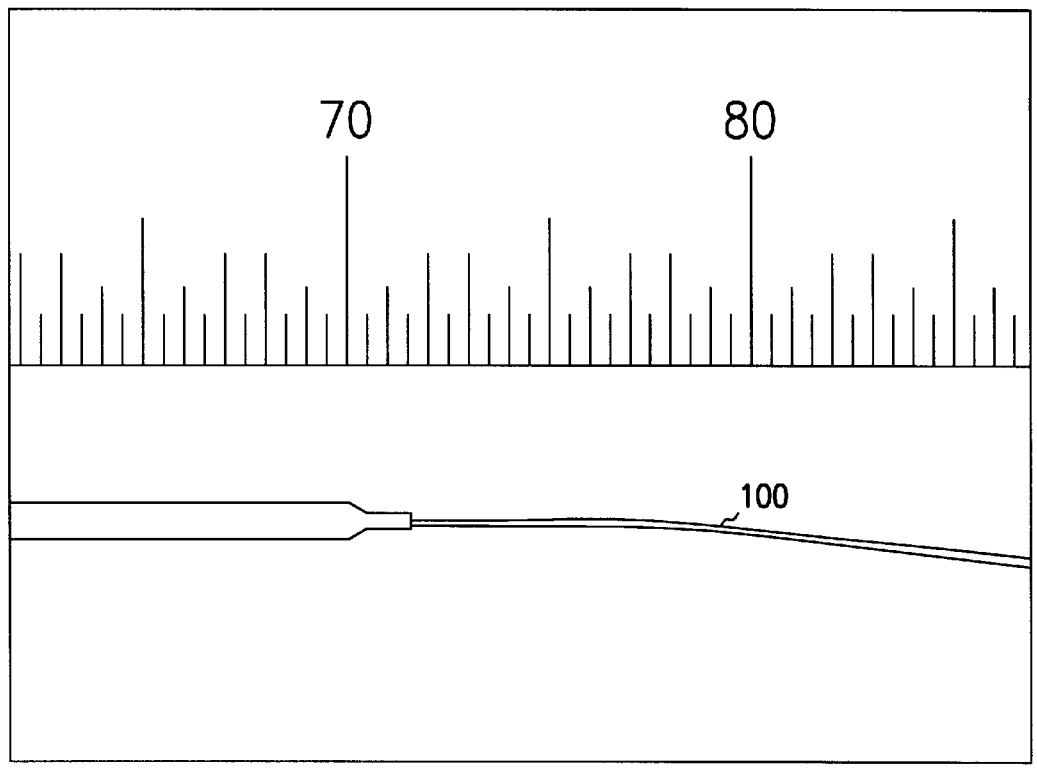
FIG. 11B is a top view of the embodiment of 11A with the clot disrupting loop in an undeployed position.
Figure 11C:
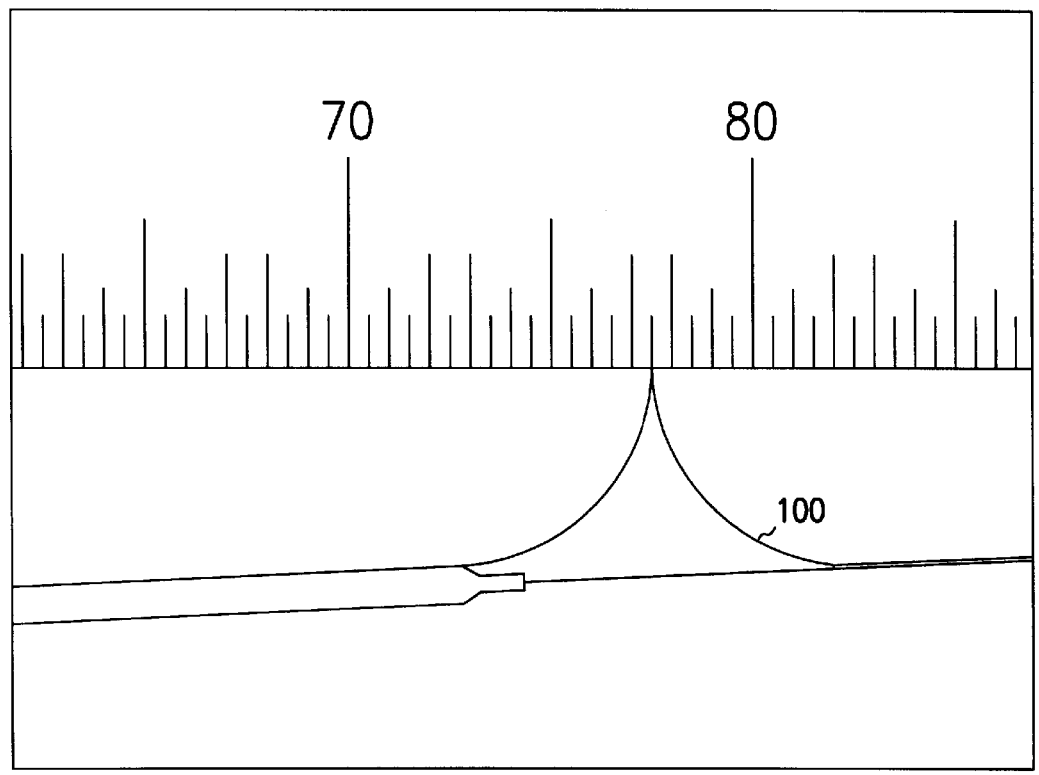
FIG. 11C is a top view of the embodiment of 11A in a partially deployed position.
Figure 11D:
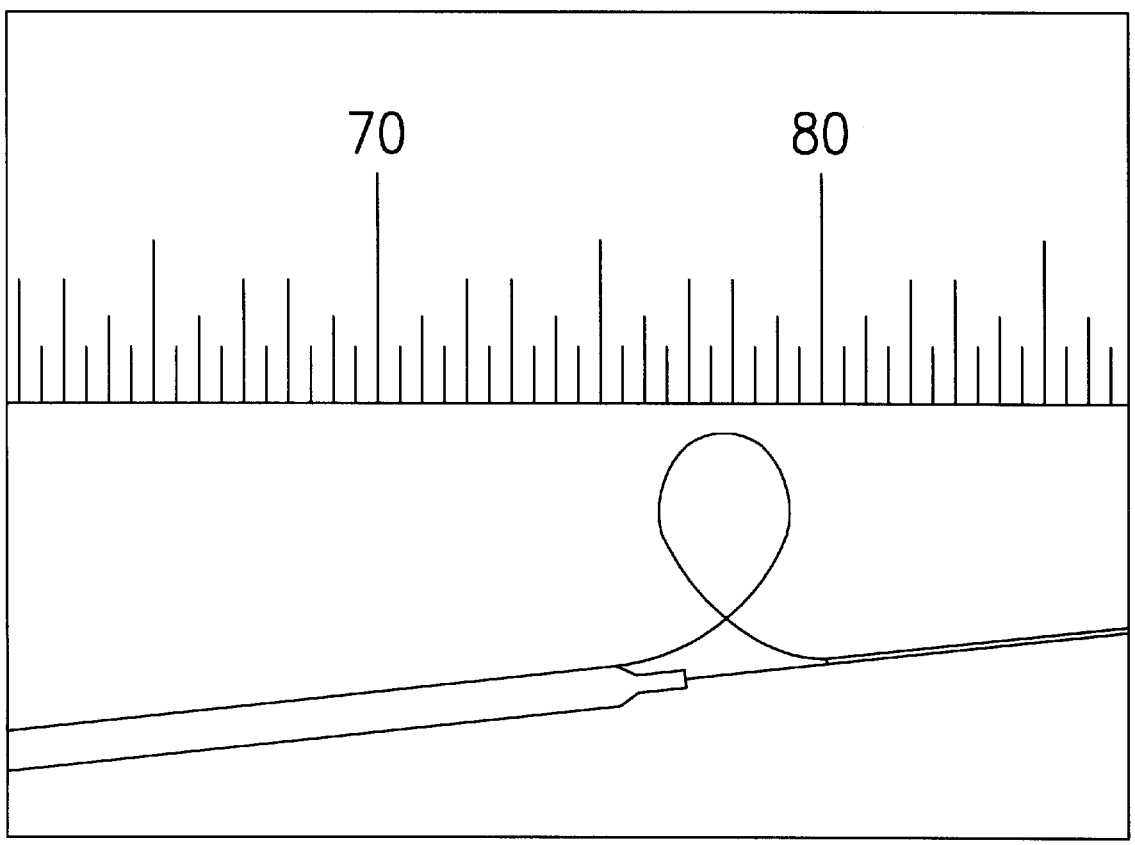
FIG. 11D is a top view of the embodiment of 11A in a fully deployed position.

In one other thrombus disrupting embodiment, illustrated at 100 in FIG. 11, a core wire 102 is passed through a sleeve 104. A distal wire 106 is attached to the core wire 102 at 108 and to the sleeve 104 at 110. The distal wire is looped at 112. A coiled sleeve embodiment is shown at 105 in FIG. 11A. The distal wire 106 is made of a material such as Nitinol. The thrombus disrupting embodiment 100 is advanced with the core wire 102 pushed forward and deployed by pulling backward and opening within a thrombus. The device 100 is shown in an undeployed position in FIG. 11B. The device 100 is shown in a partially deployed position in FIG. 11C and in a fully deployed position in FIG. 11D.

Figure 12A:
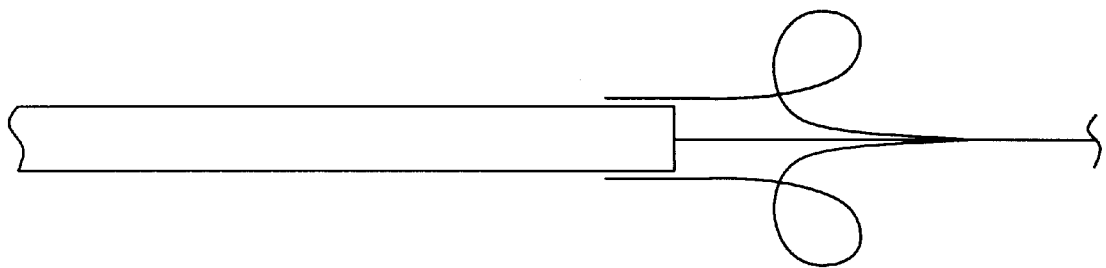
FIG. 12A is a side view of a dual loop embodiment of the clot disrupting device of the present invention.
Figure 12B:
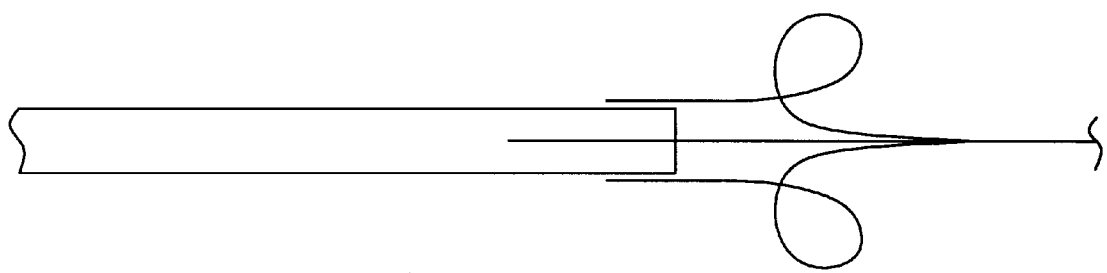
FIG. 12B is a side view of another three or more loops-based embodiment of the clot disrupting device of the present invention.
Figures 1, 12C:
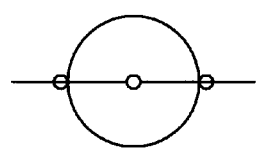
FIG. 12C is a top view of a dual loop embodiment of FIG. 12A.
Figures 1, 12D:
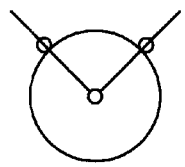
FIG. 12D is a radial top view of the loop embodiment of FIG. 12B.
Figures 1, 12E:
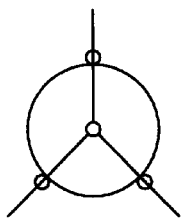
FIG. 12E is a an alternate view of a triple loop embodiment of the clot disrupting wire of the present invention.
Figures 1, 12F:
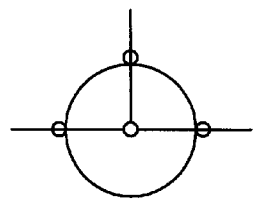
Figure 12C:
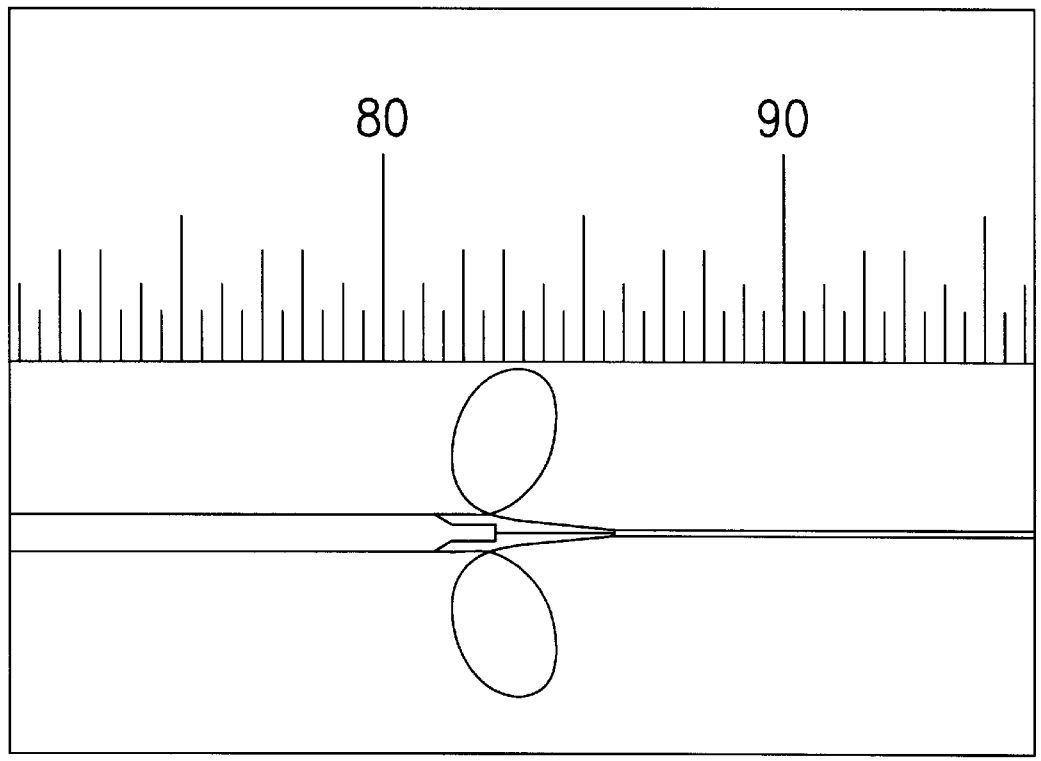
Figure 12D:
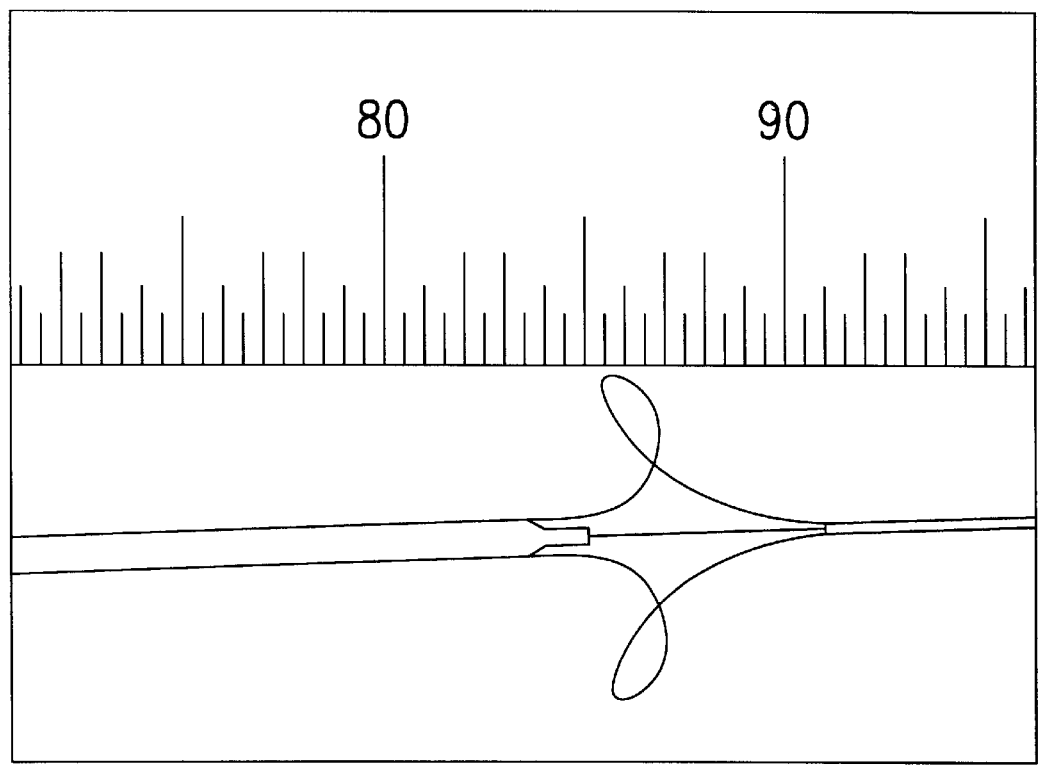
Figure 12E:
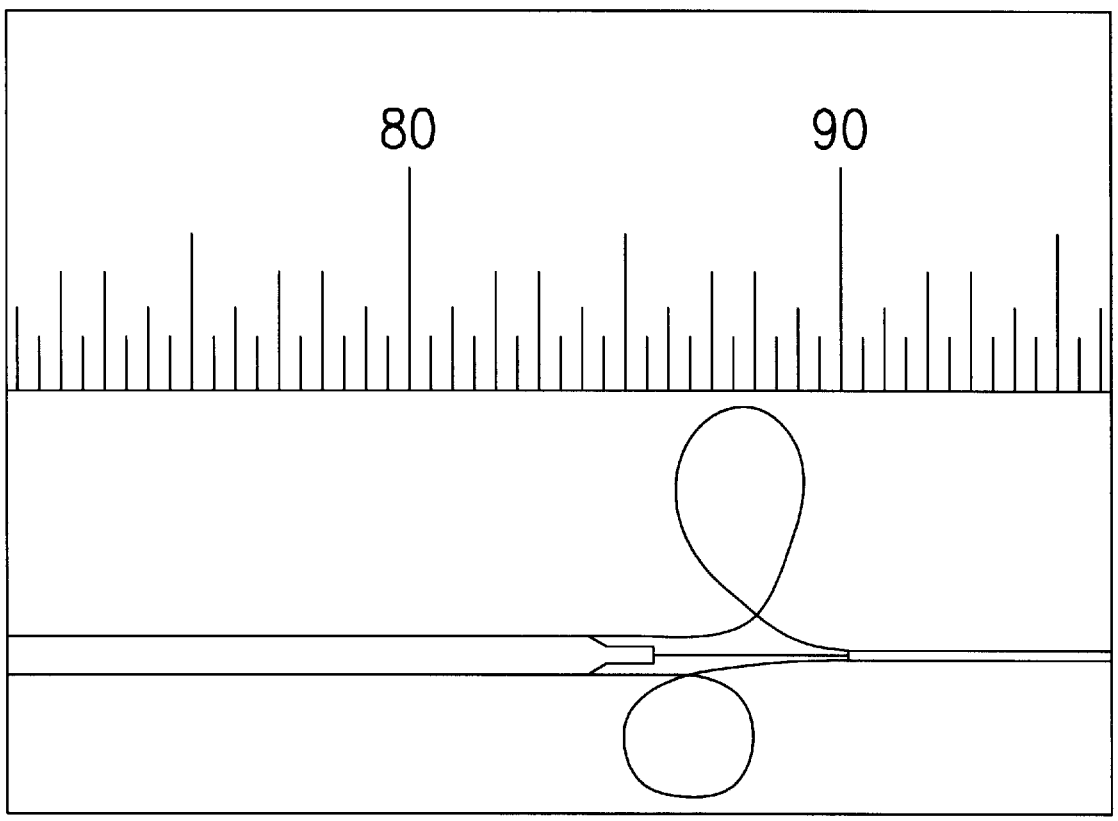

The Nitinol distal wire 106 is bonded to the core wire 102 and the sleeve 104 by gluing, welding, soldering or by oversleeving with PTFE or polyester. Multiple loop embodiments are shown in FIGS. 12A, 12B, 12C 12D, 12E and 12F. The multiple loop embodiments vary the number of wires and the positioning on the sleeve 102 as shown in FIGS. 12C and 12D (two wires) and in FIGS. 12E and 12F (three wires).

Figure 13:
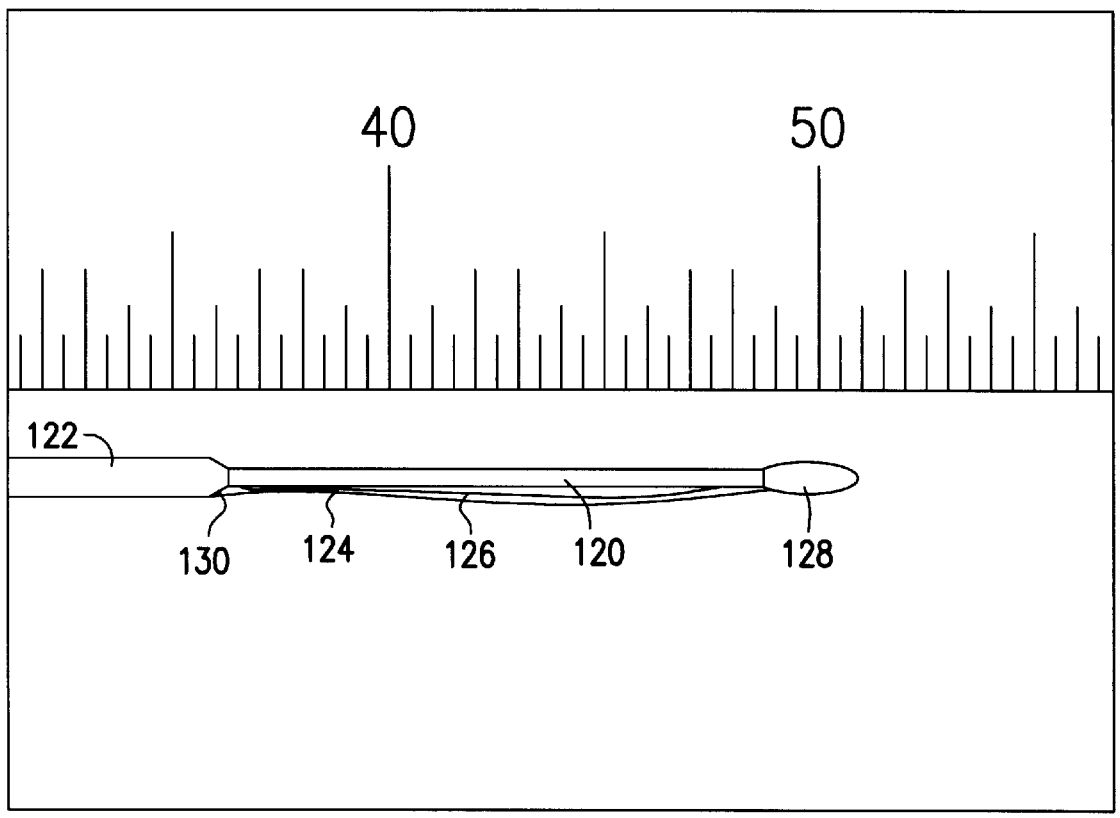
FIG. 13 is a top view of another clot disrupting wire embodiment of the present invention, such as FIG. 6, in an undeployed position.
Figure 13A:
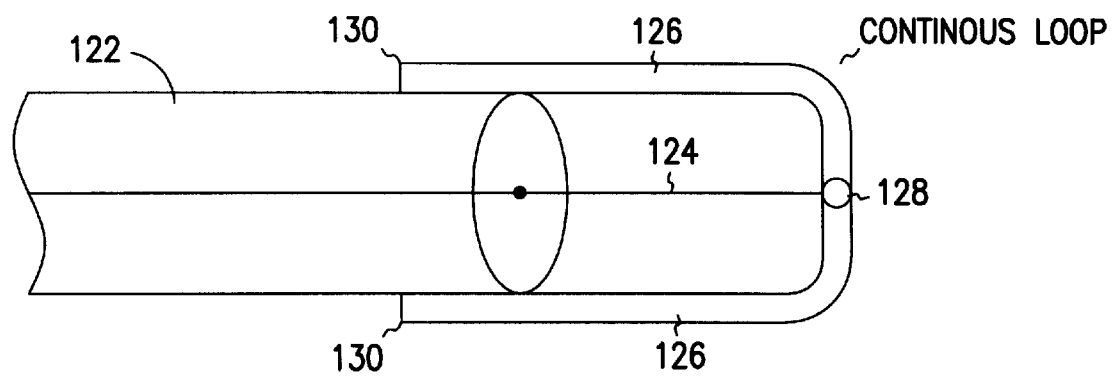
FIG. 13A is a side view of an alternate macerating wire embodiment of FIG. 13.
Figure 14:
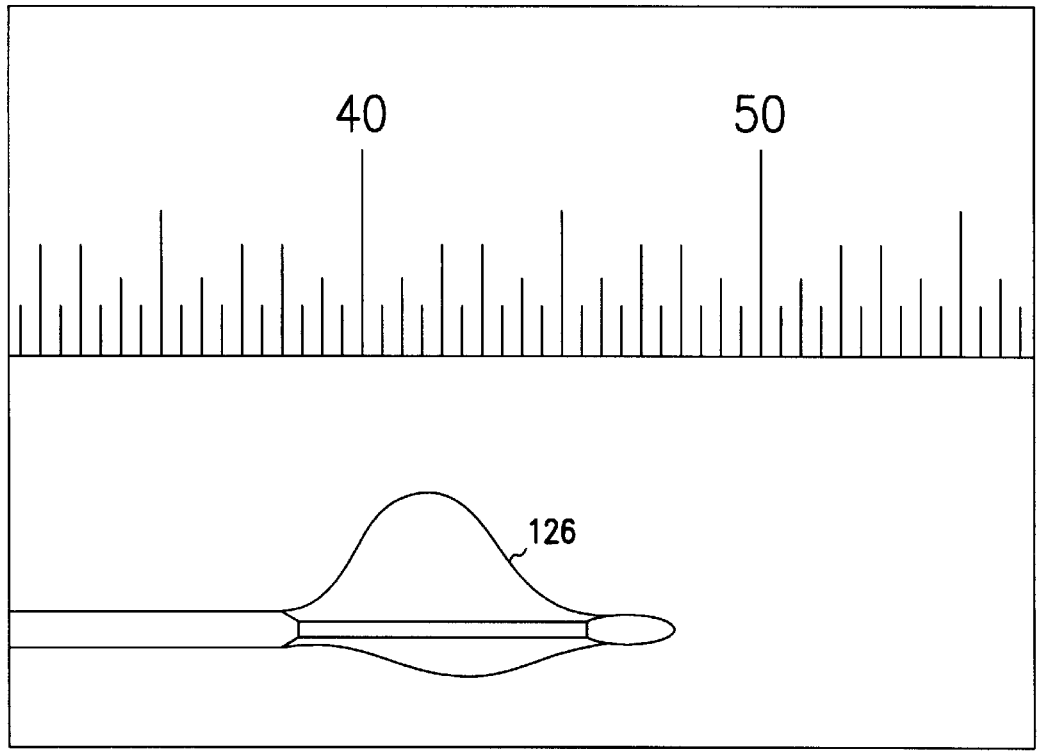
FIG. 14 is a top plan view of the clot disrupting wire embodiment of FIG. 13 in a partially deployed position.
Figure 15:
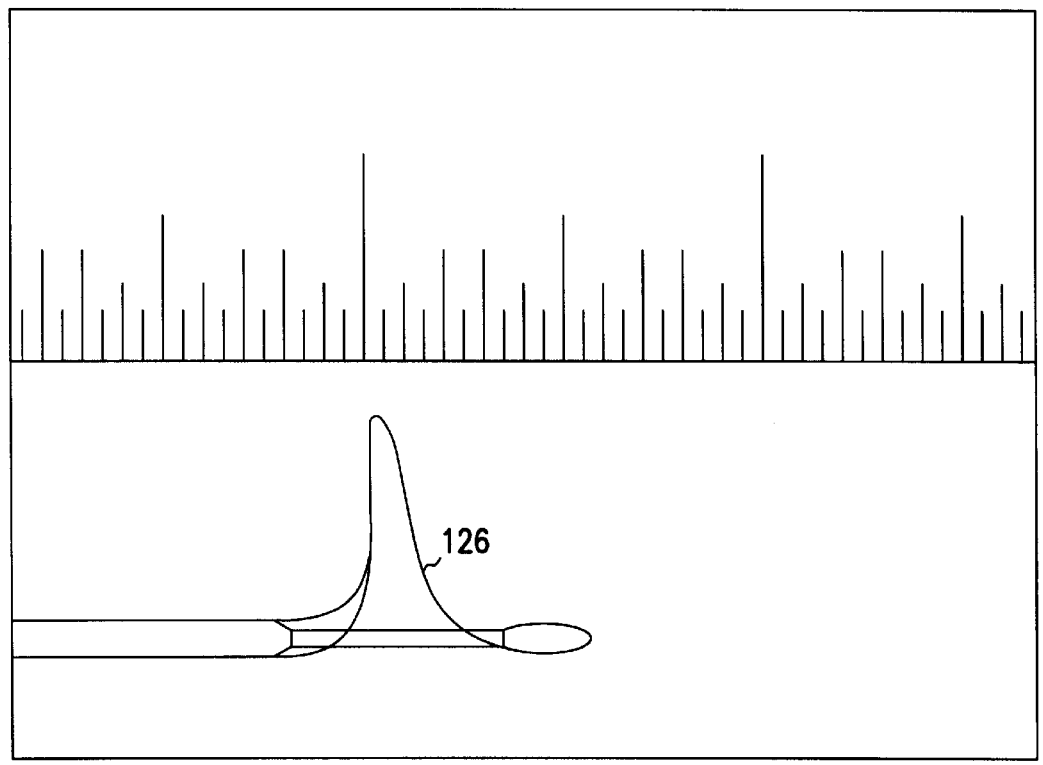
FIG. 15 is a top plan view of the clot disrupting wire embodiment of FIG. 13 in a fully deployed position.

Another thrombus disrupting assembly embodiment illustrated at 120 in FIG. 13 in an undeployed position includes a sleeve 122 and a core wire 124 positioned within the sleeve 122. A distal wire 126 is attached to the core wire at 128 and to the sleeve 122 at 130. As the core wire 124 is pulled, the distal wire 126 is expanded as shown in a partially deployed position in FIG. 14. The thrombus disrupting loop embodiment 120 is fully expanded and deployed in FIG. 15.

The thrombus disrupting assembly embodiments described herein may include discrete serrated regions or a continuous serrated region that extends along the entire loop or loops. As appropriate, the core wire may be serrated or have scoops on it.

Figure 16:
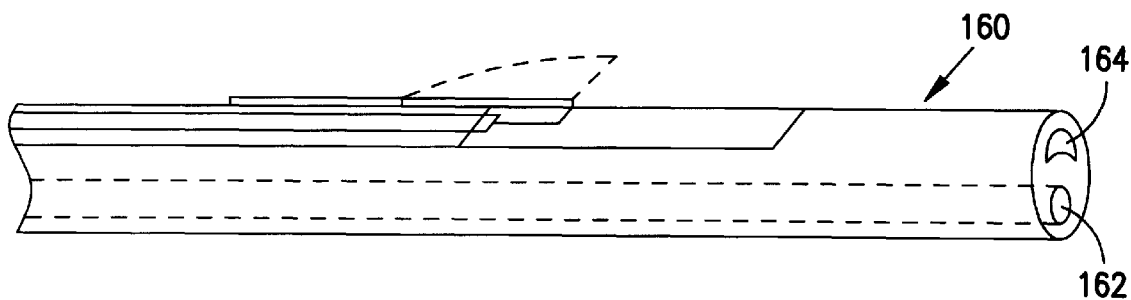
FIG. 16 is a side view of one embodiment of the side deployed skived dual lumen catheter device of the present invention.
Figure 17:
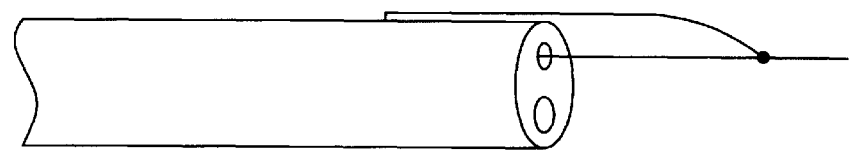
FIG. 17 is a side view of another embodiment of the dual lumen catheter device of the present invention.
Figure 18:
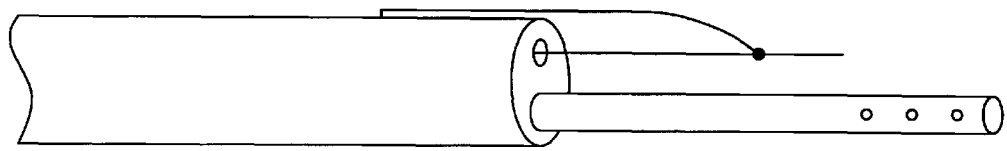
FIG. 18 is a side view of an embodiment of a dual lumen catheter device with an extended infusion tip.

The macerating assembly embodiments may be used in conjunction with a guide that permits insertion of the wire/catheter assembly into a microcatheter or catheter of an inner ID of 0.021 inches or greater. In one other embodiment, illustrated generally at 130 in FIG. 13, the clot disrupting wire assembly 10 is positioned with or is integral to a dual lumen catheter. The dual lumen catheter permits concurrent thrombus disruption and drug delivery to a thrombus. A side view of one embodiment of the duel lumen catheter type device of the present invention is illustrated at 160 in FIG. 16. One of the thrombus disrupting assemblies described herein is positioned within lumen 162. A lumen 164 may be used for drug delivery. The thrombus disrupting assembly may be out of a side-hole assembly as shown in FIG. 16 or out of the end of the catheter as shown in FIG. 17. The infusion lumen may be extended beyond the macerator as shown in FIG. 18 and infusion may be performed through an endhole or through side ports.

An addition of a "bumper" tip for added purchase or/and tracking of the device may be added to any of these. This bumper tip may be a soft polymer, a coiled tip or any other extension beyond the current site of action of the device.

Those skilled in the art will further appreciate that the present invention may be embodied in other specific forms without departing from the spirit or central attributes thereof. In that the foregoing description of the present invention discloses only exemplary embodiments thereof, it is to be understood that other variations are contemplated as being within the scope of the present invention. Accordingly, the present invention is not limited in the particular embodiments which have been described and detailed herein. Rather, reference should be made to the appended claims as indicative of the scope and content of the present invention.

What is claimed is:

1. An assembly for clot disruption, comprising:
   an annular sleeve;
   a core wire positioned within the annular sleeve; and
   a distal end wire attached to the annular sleeve and the core wire wherein the distal end wire is movably positionable within the annular sleeve, extending from the core wire, and outside of the annular sleeve, having a shape comprising a bend or an M-shape or a loop.

2. The assembly of claim 1 wherein the distal end wire comprises a bend proximal to the sleeve.

3. The assembly of claim 1 wherein the distal end wire comprises a bend distant from the sleeve.

4. The assembly of claim 1 wherein the distal end wire is a shape memory wire.

5. The assembly of claim 1 wherein the core wire is attached to one end of the distal wire.

6. The assembly of claim 1 wherein the core wire is attached to a mid point of the distal wire.

7. The assembly of claim 1 wherein the distal wire forms more than one loop.

8. The assembly of claim 1 and further comprising an insert for insertion into a catheter or microcatheter.

9. The assembly of claim 1 and further comprising a dual lumen catheter wherein the thrombus disrupting wire assembly is positioned within one lumen.

10. The assembly of claim 1 wherein the sleeve, core wire and distal end wire are sized for clot disruption in the brain.

11. The assembly of claim 1 and further comprising a mechanism at a proximal end of the core wire for movement of the core wire or distal end wire.

12. The assembly of claim 11 wherein the mechanism comprises handles or grippers in communication with the core wire.

13. The assembly of claim 1 wherein the core wire comprises at least one serration.

14. The assembly of claim 1 wherein the distal end wire comprises at least one serration.

15. The assembly of claim 1 wherein one or more of the distal end wire and core wire is coated with a coating.

16. The assembly of claim 15 wherein the coating comprises one or more of an abrasive coating or a hydrophilic coating or a coating comprising a lytic drug.

17. The assembly of claim 1 wherein the distal end wire is capable of radial expansion.

18. A method for clot disruption, comprising:

providing a clot disrupting assembly that comprises an annular sleeve, a core wire positioned within the annular sleeve and a distal end wire attached to the annular sleeve and the core wire wherein the distal end wire is movably positionable within the annular sleeve, extending from the core wire, and outside of the annular sleeve, having a shape comprising a bend or an M-shape or a loop;

pushing the core wire in order to deploy the distal end wire; and positioning the distal end wire within the clot.

19. A method for clot disruption, comprising:

Providing a clot disrupting assembly that comprises an annular sleeve, a core wire positioned within the annular sleeve and a distal end wire attached to the annular sleeve and the core wire wherein the distal end wire is movably positionable within the annular sleeve, extending from the core wire, and outside of the annular sleeve, having a shape comprising a bend or an M-shape or a loop;

Pulling the core wire in order to deploy the distal end wire; and

Positioning the distal end wire within the clot.

20. The methods of claims 18 or 19 wherein the clot disruption is a recannulization.

21. The methods of claims 18 or 19 and further comprising infusing a lytic drug into the clot.

22. A kit for clot disruption, comprising:

A catheter comprising a main body defining a first lumen and a second lumen; and A clot disrupting assembly comprising an annular sleeve, a core wire positioned within the annular sleeve and a distal end wire attached to the annular sleeve and the core wire wherein the distal end wire is movably positionable within the annular sleeve, extending from the core wire, and outside of the annular sleeve, having a shape comprising a bend or an M-shape or a loop.

23. The kit of claim 22 and further comprising a drug delivered in the second lumen.

24. The kit of claim 22 and further comprising a macerater positioned in the second lumen.

* * * * *